United States Patent [19]

Schwartz

[11] Patent Number: 4,689,307
[45] Date of Patent: Aug. 25, 1987

[54] FLUORESCENCE MICROSCOPY SAMPLE MOUNTING METHOD AND STRUCTURE

[75] Inventor: Abraham Schwartz, Durham, N.C.

[73] Assignee: Caribbean Microparticles Corporation, Hato Rey, P.R.

[21] Appl. No.: 902,609

[22] Filed: Sep. 2, 1986

[51] Int. Cl.[4] ............................................. G01N 31/00
[52] U.S. Cl. ............................................ 436/8; 436/19
[58] Field of Search ........................................ 436/8–19; 252/408.1, 315.01

[56] References Cited

U.S. PATENT DOCUMENTS 4,020,006 4/1977 Parker ..................................... 436/8
4,461,718 7/1984 Kaye et al. ............................. 436/19

Primary Examiner—Deborah L. Kyle
Assistant Examiner—T. J. Wallen
Attorney, Agent, or Firm—B. B. Olive; Steven J. Hultquist

[57] ABSTRACT

A method and structure for mounting fluorescent samples, e.g., fluorescent microbeads, are based on immobilizing the samples in a gel which preserves the spectral properties of the samples and mounting the gel containing the samples on a slide and beneath a coverslip.

8 Claims, 2 Drawing Figures

FLUORESCENCE MICROSCOPY SAMPLE MOUNTING METHOD AND STRUCTURE

FIELD OF THE INVENTION

This invention relates to a method of and structure for mounting fluorescent samples to immoblize the samples without altering their spectral properties. More specifically, the invention relates to fluorescent microbead standards that are mounted on microscope slides in such a way that they are immobilized while maintaining their spectral properties as when in free suspension.

BACKGROUND ART

As described in copending patent application Ser. No. 06/685,464, filed Dec. 24, 1984, entitled "Calibration Method For Using Fluorescent Microbeads And Synthesis Thereof", microbeads can be produced which not only have the size of biological cells, but also have the fluorescent excitation and emission properties, i.e., the spectral properties of stained cells. Maintaining these properties is extremely important when using these microbeads as standards for performing quantitative fluorescence measurements. However to retain these properties, it is necessary to keep the microbeads in the same environment as that in which the stained cells are held. This is because the fluorescent dyes associated with the microbeads, e.g. fluorescein, are very sensitive to environmental conditions such as solvent and pH. Moreover, when observing a suspension of these microbeads which have been placed on a glass slide with a cover slip under a microscope they are found to be highly mobile within the aqueous suspending solution. This mobility make these microbeads very difficult to photograph and to quantitatively measure their size and fluorescence intensities. Furthermore with time, these mounts dry out leaving the microbeads in air which changes their spectral properties.

DISCLOSURE OF THE INVENTION

The invention provides a mounting media and mounting procedure which allows fluorescent samples, specifically microbeads, on a microscope slide to be immobilized while still retaining the spectral properties they possess when in free solution. To the mounting media in which the microbeads are normally suspended is added a small percentage of non-fluorescent material which causes the media containing the microbeads to gel under certain described conditions. When suspended in the gel, the microbeads are immobilized but are still in contact with the same aqueous environment as they were when in free suspension and thus exhibit the same spectral properties.

BEST MODE FOR CARRYING OUT THE INVENTION

Figure 1:
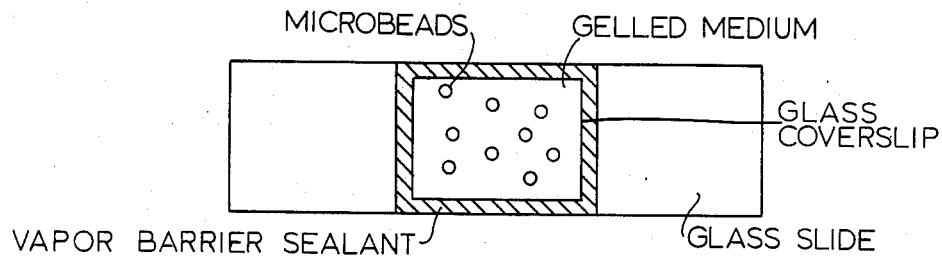
FIG. 1 is a plan view of a slide mounted according to the invention.
Figure 2:
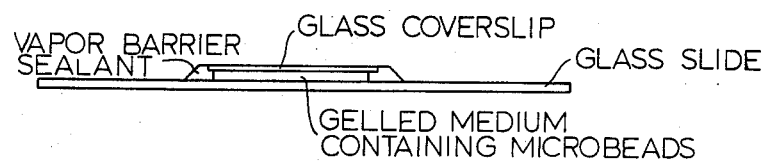
FIG. 2 is an elevation view of the slide shown in FIG. 1.

Gelation materials suitable for the invention must be colorless when in solution, non-fluorescent at the wavelengths used during observation and measurement, completely miscible in the suspending solution, and not have any physical or chemical effect on the microbeads. Materials suitable for such use are special polymers of high molecular weight. For aqueous solutions such high polymers include gelatin, starch, algenate, and dextran. Concentrations of 0.1 to 5% by weight of these materials in solution have been found to be useful in the invention. To form the solutions, it is desirable to heat the solution until the mentioned polymer materials are completely dissolved, i.e., such that there is a very little tindle light scattering in the solution. The microbeads are mixed into the warm solution, placed on a microscope slide, cover-slipped and allowed to cool. While warm, the mounting media containing the microbeads flows freely. During this process it has been observed that all of the microbeads settle to the surface of the glass slide thus placing them in the same focal plane, i.e., on top of the glass slide. Upon cooling to room temperature the media gels and immobilizes the microbeads. The resulting slide structure is illustrated in FIGS. 1 and 2.

It has been found that the gel can be prevented from drying out over time by sealing the edges of the cover slip with a material which is impervious to water vapor. A bead of either epoxy resin or silicone rubber is deemed suitable for establishing a vapor barrier to water loss from the gel. Once the sealent material is dried, the slides can be used as with any normal slide mount with the exception of keeping them in the dark when not in use. This prevents possible photobleaching, i.e., a decrease in fluorescent intensity of the fluorescent samples. A specific example is next given.

EXAMPLE

To a solution at pH 7.2 containing 0.1 m NaCl, 0.05 M phosphate, 0.5% bovine serum albumin, and 0.5% Na Azide was added 5% gelatin by weight and the solution stirred and heated to 60° C. for 10 minutes. The resulting clear solution was allowed to cool to 45° C. into which 7.5u fluorescein and R-phycoerythrin microbeads were dispersed. Ten microliters of this warm microbead suspension were placed on a glass microscope slide and coverslipped as illustrated in FIGS. 1 and 2. The suspension completely spread under the coverslip and gelled within 30 minutes at room temperature. The edges of the coverslip were sealed with a bead of epoxy resin and allowed to set overnight. Upon examination under a fluorescence microscope, the microbeads were found to be completely immobilized and the fluorescein and R-phycoerythrin microbeads were found to have the same spectral properties they have in free aqueous solution, i.e., under blue excitation, the fluorescein microbeads were green and the R-phycoerythrin microbeads were orange. Thus, the object of the invention was achieved.

What is claimed is:

1. A method of fabricating fluorescent samples comprising the steps of:
    (a) forming a first solution comprising a non-fluorescent media in which selected fluorescent samples when freely suspended therein exhibit defined fluorescent spectra;
    (b) adding to said first solution a non-fluorescent additive to provide a second solution, said additive being effective under selected conditions to cause said media to gel;
    (c) combining with said second solution a selected quantity of said fluorescent samples under first conditions such that said samples are freely suspended;

(d) placing said second solution containing said freely suspended fluorescent samples on a microscope slide beneath a coverslip;

(e) subjecting said second solution on said slide to second conditions effective to cause said second solution to gel and thereby immobilize said samples in the gel, said immobilized samples exhibiting substantially the same said defined fluorescent spectra as when freely suspended in said first solution.

2. A method as claimed in claim 1 including the step of sealing the edges of said coverslip to said slide with a vapor barrier material.

3. A method as claimed in claim 2 wherein said samples comprise fluorescent microbeads.

4. A method as claimed in claim 1 wherein said samples comprise fluorescent microbeads.

5. A method as claimed in claim 1 wherein said additive comprises a gelatin and said first conditions include heating and said second conditions include cooling said second solution.

6. A method as claimed in claim 1 wherein said first conditions comprise one set of conditions for forming said second solution with said additive and said second conditions comprise another set of conditions for causing said gel to be established.

7. A fluorescent sample structure comprising:
  (a) a sample composition comprising
    (i) fluorescent samples having a defined fluorescent spectra when freely suspended in a selected media; and
    (ii) a gel formed by said media and an additive effective to cause said media to gel, said samples being immobilized in said gel;
  (b) a transparent slide mounting said gel containing said immobilized samples; and
  (c) a coverslip over said immobilized samples.

8. A structure as claimed in claim 7 including a vapor barrier sealing the edes of said coverslip to said slide.